United States Patent [19]

Mills

[11] Patent Number: 4,510,241
[45] Date of Patent: Apr. 9, 1985

[54] PEPTIDE-TYPE SUBSTRATES USEFUL IN THE QUANTITATIVE DETERMINATION OF ENDOTOXIN

[75] Inventor: Donald F. Mills, University City, Mo.

[73] Assignee: Mallinckrodt, Inc., St. Louis, Mo.

[21] Appl. No.: 507,596

[22] Filed: Jun. 24, 1983

Related U.S. Application Data

[62] Division of Ser. No. 298,994, Sep. 3, 1981, Pat. No. 4,406,832.

[51] Int. Cl.$^3$ .................. C12Q 1/38; C12Q 1/00; C12Q 1/04; C12Q 1/06
[52] U.S. Cl. ...................................... 435/23; 435/4; 435/34; 435/39; 436/502
[58] Field of Search ................ 435/4, 7, 23, 24, 34, 435/39; 436/502

[56] References Cited

U.S. PATENT DOCUMENTS

| | | | |
|---|---|---|---|
| 4,028,318 | 6/1977 | Aurell et al. | 260/112.5 R |
| 4,056,519 | 11/1977 | Bobbitt et al. | 435/23 |
| 4,137,225 | 1/1979 | Ekenstam et al. | 260/112.5 R |
| 4,147,692 | 4/1979 | Nagatsu | 435/24 |
| 4,155,916 | 5/1979 | Smith et al. | |
| 4,167,449 | 9/1979 | Gargiulo et al. | 435/16 |
| 4,188,264 | 2/1980 | Iwanaga et al. | 435/23 |
| 4,207,232 | 6/1980 | Claeson et al. | 435/23 |
| 4,214,049 | 7/1980 | Ekenstam et al. | 435/23 |
| 4,216,142 | 8/1980 | Ali | 260/112.5 R |
| 4,217,269 | 8/1980 | Cole | 260/112.5 R |
| 4,221,706 | 9/1980 | Ali et al. | 435/23 |
| 4,229,528 | 10/1980 | Smith et al. | 435/23 |
| 4,252,715 | 2/1981 | Aurell et al. | 435/4 |

FOREIGN PATENT DOCUMENTS

| | | |
|---|---|---|
| 41089 | 12/1981 | European Pat. Off. |
| 2740323 | 10/1979 | Fed. Rep. of Germany |
| WO79/00602 | 8/1979 | PCT Int'l Appl. ............... 435/4 |

OTHER PUBLICATIONS

Iwanaga et al, Hemostasis, 7, 183–188, (1978).
Iwanaga et al, Chemical Abstract, 89: 209825e, p. 121, (1978).
Harada et al, Chemical Abstracts, 94: 151160u, p. 152, (1981).
Harada et al, Biomedical Applications of the Horseshoe Crab (Limulidae), Alen R. Liss, Inc., N.Y., 209–220, (1979).
Nakamura et al, J. Biochem., 81: 1567–1569, (1977).
Nakamura et al, Chemical Abstracts, 87: 49370f, p. 153, (1977).

*Primary Examiner*—Esther M. Kepplinger
*Attorney, Agent, or Firm*—Bernard, Rothwell & Brown

[57] ABSTRACT

Disclosed are chromogenic or fluorogenic peptide-type compounds adapted for use in determining endotoxin in a sample by a Limulus amebocyte lysate-type assay. The compounds have the general formula:

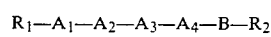

$$R_1—A_1—A_2—A_3—A_4—B—R_2$$

wherein $R_1$ represents hydrogen, a blocking aromatic hydrocarbon or acyl; $A_1$ represents an L or D-amino acid selected from either Ileu, Val or Leu; $A_2$ represents Glu or Asp; $A_3$ represents Ala or Cyst; $A_4$ represents Arg, B represents a linkage group selected from ester and amide linkage groups; and $R_2$ represents a chromogenic or fluorogenic group which is covalently attached to the C-carboxyl terminal of arginine through the B linkage group and which yields a chromophoric or fluorescent marker compound of the formula $R_2$—B—H upon enzymatic hydrolysis from the remainder of the peptide-type compound by activated LAL pro-clot enzyme. Also disclosed are methods for the determination of endotoxin in a sample by contacting the sample with a pro-clotting enzyme from Limulus amebocyte lysate and one of the above chromogenic or fluorogenic peptide-type compounds.

9 Claims, No Drawings

PEPTIDE-TYPE SUBSTRATES USEFUL IN THE QUANTITATIVE DETERMINATION OF ENDOTOXIN

This is a division of application Ser. No. 298,994, filed Sept. 3, 1981, U.S. Pat. No. 4,406,832.

The present invention relates generally to peptide-type compounds and, more particularly, to peptide-type compounds adapted for use as chromogenic or fluorogenic substrates in the quantitative determination of a lipopolysaccharide activated pro-clot enzyme found in the amebocyte lysate of the blood of horseshoe crabs such as *Limulus polyphemus* and other related species.

The coagulation phenomena of the pro-clotting enzyme of the amebocyte lysate from the blood of the horseshoe crab by bacterial endotoxin has been known and reported for many years, see, for example, Levin, J. and Bangs, F. B., "Clottable Protein in Limulus: Its Localization and Kinetics of its Coagulation by Endotoxin", Thomb. Diath. Haemorrh., 19, pg. 186 (1968). However, it has been only recently that the clotting mechanism has been subjected to in-depth studies such as the study by Nakamura, S., et al., "Amino Acid Sequence Studies on the Fragments Produced from Horseshoe Crab Coagulogen during Gel Formation: Homologies with Primate Fibrinopeptide B", Biochemical and Biophysical Research Communication, 72(3), p. 902 (1976). Such studies have demonstrated that the coagulation of Limulus amebocyte lysate, hereinafter LAL, involves the endotoxin activation of a pro-clot enzyme in the presence of divalent cations, e.g., $Ca++$, $Mg++$, $Sr++$ or $Mn++$, with the resulting activated enzyme cleaving a clotting protein (coagulogen) at the C-carboxyls of contained glycine and arginine units. The cleaved units of the coagulogen remain attached by disulfide bridges and undergo polymerization to effect a clot. In addition to these known components of the amebocyte lysate, there are many other proteins and a known inhibitor of a lipoprotein nature. The modulation of the coagulation reaction by the inhibitor and other proteins has not as yet been determined.

Because of the coagulation characteristic of LAL in the presence of bacterial endotoxin (pyrogen), LAL formulations have become commercially important reagents for use in quality control endotoxin assays in the manufacture of various fluids of pharmaceutical/medical interest which are normally administered parenterally. Such fluids include water for injection; water for irrigation; lipid emulsions for intravenous feeding; aqueous emulsions of vegetable oil; salt solutions, e.g., parenterally administered sodium chloride solutions including sodium chloride for injection USP, sodium chloride for irrigation USP, sodium chloride for inhalation, and lactated Ringer's solution; and blood derivatives, e.g., normal serum albumin, plasma protein fraction and anti-hemophilic factor USP, immune globulin, Rho(D) immune globulin and antihuman globulin serum.

The formulation of LAL reagents and the improvement in LAL procedures has progressed to the point that an LAL assay is the most sensitive and practical endotoxin test that is known. The LAL assay can detect, with the formation of a clot, as little as $10^{-12}$ grams/ml of endotoxin. It has been recently demonstrated in a Health Industries Association Study [Dabbah, et al., "HIMA Collaborative Study for the Pyrogenicity Evaluation of a Reference Endotoxin by the USP Rabbit Test", HIMA Document No. 7, Vol. 1 (May, 1979)] that the United States Pharmacopeia (USP) rabbit pyrogen assay can detect approximately $10^{-9}$ grams/ml of endotoxin. Therefore, the LAL assay is approximately 100 times as sensitive as the USP rabbit pyrogen assay. In addition to its advantage of sensitivity, the LAL assay is simpler to perform and can be completed in approximately one hour as opposed to three hours for the rabbit assay.

The use of chromogenic substrates has become a means to both study and clinically monitor various enzymes and inhibitors in the complex coagulation processes of man. An extensive list of enzyme specific substrates are commercially available for measuring enzymes such as trypsin, thrombin, thromboplastin, plasmin, plasmin Kallikrein, Urokinase, and plasminogen. These synthetic substrates provide the investigator with an important tool to monitor the hemostatic state of certain aspects of the coagulation process in vitro.

It was recently reported by Iwanaga, et al., "Chromogenic Substrates for Horseshoe Crab Clotting Enzyme: Its application for the Assay of Bacterial Endotoxin", Hemostasis 7:183–188 (1978) that synthetic substrates can be used to measure the level of endotoxin activated pro-clot enzyme in LAL prepared from the blood of both the Japanese (*Tachypleus tridentatus*) and the American (*Limulus polyphemus*) horseshoe crabs. The use of substrates in an LAL assay has certain advantages over that of a conventional LAL gelation test in that the amount of activated clot enzyme can be quantified. In addition, the use of certain synthetic peptide-type substrates to quantitatively measure bacterial endotoxins in a LAL assay has been described in U.S. Pat. No. 4,188,264. The disclosure of the patent states that the peptide substrate must have a structure consisting of L-amino acids which are linked in a proceeding order of arginine to glycine in which arginine is the C-carboxyl terminal amino group in order to be cleaved by the activated pro-clot enzyme.

While the above described substrates find utility in LAL-type assays for endotoxin, it is desirable to develop additional substrates for the quantitative determination of endotoxin. Such substrates should have a number of characteristics including the ability to be readily cleaved by activated LAL pro-clot enzyme in a reproducible and proportional manner. Due to unknown and intricate mechanism by which the pro-clot enzyme is activated and the uncertain nature by which the enzyme acts in cleavage reactions, it is difficult, if not impossible, to predict whether a particular substrate will function in the desired manner in an LAL-type assay.

The peptide compounds encompassed by the present invention are characterized by having the following formula:

$$R_1-A_1-A_2-A_3-A_4-B-R_2$$

wherein $R_1$ represents hydrogen, or a blocking aromatic hydrocarbon or acyl; $A_1$ represents an L or D-amino acid selected from either isoleucine (Ileu), valine (Val) or leucine (Leu); $A_2$ represents glutamine (Glu) or aspartine (Asp); $A_3$ represents alanine (Ala) or cysteine (Cys); $A_4$ represents arginine (Arg), B is an amide or ester linkage, and $R_2$ represents a chromogenic or fluorogenic group which is covalently attached to the C-carboxyl terminal of arginine through the amide or ester linkage and which yields a chromophoric or fluorescent marker compound of the formula $R_2-B-H$ upon enzymatic hydrolysis from the remainder of the peptide-type compound by activated LAL pro-clot enzyme. The $R_1$ blocking group in the general formula above may be N-tert butoxycarbonyl, alkanoyl of 1 to 12 carbon atoms, cyclohexylcarbonyl, and N-benzoyl, acetyl and benzoyl substituted with one or more halogens, lower alkyl, e.g., methyl and ethyl, amino or phenyl groups, or may be H when the N-terminal L-amino acid of the peptide structure is replaced with a N-terminal D-amino acid. Suitable chromogenic or fluorogenic groups include nitrophenyl, methylnitrophenyl, dinitrophenyl, naphthyl, nitronapththyl, methoxynaphththyl, indoxyl, methylindoxyl, (4-methyl-)umbelliferyl and resorfin.

Also contemplated by the present invention are the acid addition salts of the above peptide-type compounds. Suitable acid salts include those from mineral acids such as hydrochloric, hydrobromic, hydrosulfuric and hydrophosphoric or from organic acids such as formic, acetic, oxalic, tartaric, methane sulfonic and benzene sulfonic.

As was set forth previously, the peptide-type compounds of the subject invention are useful as chromogenic or fluorogenic substrates in an LAL-type assay. During such an assay, the pro-clot enzyme (a serine protease) in the LAL is activated by endotoxin and cleaves the peptide chain on the C-carboxyl of arginine so as to release the chromogenic or fluorogenic group and form a marker compound which can be easily read by means such as spectrophotometry.

In view of the criteria set forth in U.S. Pat. No. 4,188,264 set forth above, it was unexpected that substrates having either alanine or cysteine adjacent to arginine in the peptide linkage could be used in an LAL assay without affecting the ability of the activated LAL clotting enzyme to cleave the chromophoric or fluorophoric group from the C-terminal of arginine. Furthermore, the ability of the subject substrates to be cleaved by the activated LAL clotting enzyme could not be predicted since the intricate mechanism by which the pro-clotting enzyme is activated is not clearly understood. Among the problems in comprehending the mechanism is that the enzyme is classified as a protease, but apparently acts as an amidase in the cleavage of the fluorogenic or chromophoric group from the peptide.

Particularly preferred peptide-type compounds in accordance with the present invention include the following:

Benzoyl-L-Isoleucyl-L-Glutamyl-L-Alanyl-L-Arginyl-p-nitroanilide
Benzoyl-L-Isoleucyl-L-Glutamyl-L-Alanyl-L-Arginyl-4-Methoxy-β-naphthylamide
Benzoyl-L-Isoleucyl-L-Glutamyl-L-Cysteinyl-L-Arginyl-p-nitroanilide
Benzoyl-L-Isoleucyl-L-Glutamyl-L-Cysteinyl-L-Arginyl-4-Methoxy-β-naphthylamide Synthesis of the peptide-type compounds of this invention may use protective group and coupling methodologies which are known to those knowledgeable in the field of peptide chemistry, see, e.g., Bodansky, et al., "Peptide Synthesis", Interscience Publication (1966) incorporated herein by reference. For example, the substrates of this invention can be synthesized by one of the following methods:

1. The fluorogenic group or chromogenic group ($R_2$) is coupled to arginine with the step-wise addition of the required amino acid (i.e., alanine or cysteine) to achieve the desired peptide structure. In this method, the chromogenic or fluorogenic group acts as a protective group by blocking the C-terminal carboxyl of arginine.
2. The chromogenic or fluorogenic group ($R_2$) is coupled after the complete step-wise synthesis has produced the desired peptide structure. According to this method, other well-known peptide chemistry blocking groups would be used during the step-wise synthesis and then removed just prior to the coupling of the chromogenic or fluorogenic group by a racemization-free enzymatic splitting.
3. The chromogenic or fluorogenic group ($R_2$) is coupled to arginine to form a monopeptide which is coupled to a separately synthesized tripeptide of the desired sequence. This procedure would use well known peptide chemistry blocking groups which could be removed just prior to the coupling of the mono- and tripeptide sequences.

Blocking groups commonly used in the field of peptide chemistry to protect the amino ($\alpha$-N-Amino) group of the amino acid or peptide structure include Cbo (carbobenzoxy), MeOCbo (p-Methoxycarbobenzoxy), $NO_2$ Cbo (p-nitrocarbobenzoxy), BOC (tert-butoxycarbonyl), TFA (trifluoroacetyl), formyl, tosyl and ethylmercapto ester. Activation of the $\alpha$-carboxy group of the amino acid can be accomplished by preparing the p-nitrophenyl ester, trichlorophenyl ester, pentachlorophenyl ester, or N-hydroxysuccinimide ester, acid azide or acid anhydrides which may be symmetrical or asymmetrical. Additionally, it may be activated with a carbodiimide such as N,N'-dicyclohexylcarbodiimide. Generally, when blocking groups are used, the $\alpha$-N-amino group is the L-form.

Reactive groups of the amino acids that do not participate in the formation of the peptide bonds must generally be protected such as by protecting groups during the step-wise synthesis of the desired peptide. Suitable methods are common to peptide chemistry and may include the protection of the guanidino group of arginine by $NO_2$ or p-toluenesulphonyl or by protonation; the protection of the $\alpha$-OH group of glutamic by the formation of a methyl or benzyl ester or p-methoxybenzyl or allyl; and the protection of the $\beta$-SH group of cysteine by the formation of a thio ethylmercapto ester of the -SH group. It is to be understood by those knowledgeable in this field that purification at each step in the synthesis by one or both gel-filtration and crystallization is important for the successful synthesis of the desired peptide-type compound.

Furthermore, the finished, intermediate, and eluates must be subjected to stringent purity and performance tests during step-wise synthesis. The purity checks can be performed by using thin layer chromatography plates coated with silica gel F254 (Merck) as the absorption media. Gel permeation in which Sephadex ®LH-20 or G-15 can be used to separate the desired product eluate from unwanted reactants. Thin layer chromatograms can be developed in the following solvent systems:

A. Chloroform/Methanol/Acetic Acid (90:30:15)
B. n-butanol/Acetic Acid/Water (4:1:5)
C. Tetrahydrofuran/Cyclohexane/Acetic Acid/Water (186:14:10:20)
D. Chloroform/Methanol (9:1)

In addition to the TLC checks of the finished peptides for purity, their purity may be checked by High Pressure Liquid Chromatography using an UV detector and the following solvent mobile phase:

Water/methanol (50:50) in 0.01M $KH_2PO_4$ at pH 3.5–4.0.

For the sake of brevity, the following abbreviations are used in the detailed description, specific examples and claims of the subject application, and have the indicated meanings:

| | |
|---|---|
| Ala = | Alanine |
| Arg = | Arginine |
| Asp = | Aspartine |
| Cys = | Cysteine |
| Glu = | Glutamic |
| Ileu = | Isoleucine |
| Leu = | Leucine |
| Val = | Valine |
| Ac = | Acetyl |
| AcOH = | Acetic Acid |
| $Ac_2O$ = | Acetic Anhydride |
| tBOC = | Tert-butoxycarbonyl |
| Bz = | Benzoyl |
| Bzl = | Benzyl |
| $Bz_2O$ = | Benzoic Anhydride |
| Cbo = | Carbobenzoxy |
| DCCI = | Dicyclohexylcarbodiimide |
| DMF = | Dimethylformamide |
| HPLC = | High Pressure Liquid Chromatography |
| OpNP = | p-nitrophenoxy |
| pNA = | p-nitroanilide |
| TLC = | Thin Layer Chromatogram |
| TFA = | Trifluoroacetic |
| $Et_3N$ = | Triethylamine |
| HMPTA = | N,N,N',N',N'',N''—hexamethylphosphoric acid triamide |
| MeOH = | Methanol |
| $CH_2Cl_2$ = | Methylene chloride |
| THF = | Tetrahydrofuran |
| HF = | Hydrogen fluoride |
| EtOAc = | Ethyl Acetate |

Unless otherwise stated, all amino acids in the peptide structure have the L-configuration.

More specifically, substrates according to the present invention can be synthesized according to the following illustrated reaction sequence utilizing the reagents indicated. It is to be understood that N-t-butoxycarbonyl can be used in place of N-benzyloxycarbonyl as an N protecting group and that its cleavage will occur in HBr, acetic acid or TFA. TFA may also be used to cleave the N-benzyloxycarbonyl group.

SYNTHESIS REACTIONS

A. METHOD 1

1. Reaction step 1: Preparation of $N^\alpha$-Benzyloxycarbonyl-$N^\omega$-nitroarginine p-Nitrophenylamide This compound may be prepared by one of the following methods:

a. $N^\alpha$-Benzyloxycarbonyl-$N^\omega$-nitroarginine is added to a suitable solvent such as DMF, HMPTA, $CH_2Cl_2$, THF, dioxane or mixtures thereof. To this solvent system is added a suitable peptide activating agent such as either isobutyl chloroformate, or diphenylphosphoryl azide, or DCC alone or in combination with N-hydroxysuccinimide or N,N'-carbonyldiimidazole, and a suitable base such as either triethylamine, or N,N-diisopropylethylamine, or N-methylmorpholine, or pyridine, or 4-dimethylaminopyridine which may be used in combination with the other bases. To this is then added p-nitroaniline. The reaction is followed to completion by TLC or HPLC and then worked up and the product isolated in the usual manner. Purification is effected by either HPLC, gel-filtration, ion-exchange, crystallization or a combination thereof.

b. $N^\alpha$-Benzyloxycarbonyl-$N^\omega$-nitroarginine p-nitrophenyl ester is added to a suitable solvent such as DMF, HMPTA, $CH_2Cl_2$, THF, or mixtures thereof. To this is added p-nitroaniline and a suitable base such as triethylamine, N,N-diisopropylethylamine, N-methylmorpholine, pyridine or 4-dimethylaminopyridine which may be used in combination with the other bases. The reaction is followed to completion by TLC or HPLC and then worked up and the product isolated in the usual manner. Purification is effected by either HPLC, gel-filtration, ion-exchange, crystallization or a combination thereof.

c. $N^\alpha$-Benzyloxycarbonyl-$N^\omega$-nitroarginine is added to a suitable solvent such as DMF, HMPTA, $CH_2Cl_2$, THF or mixtures thereof. To this is then added a suitable base such as triethylamine, N,N-diisopropylethylamine, N-methylmorpholine, pyridine or 4-dimethylaminopyridine which may be used in combination with the other bases, and p-nitrophenylisocyanate. The reaction is followed to completion by TLC or HPLC and then worked up and the product isolated in the usual manner. Purification is effected by either HPLC, gel-filtration, ion-exchange, crystallization or a combination thereof.

2. Reaction Step 2: Preparation of N-Benzyloxycarbonylalanyl-$N^\omega$-nitroarginine p-Nitrophenylamide The $N^\alpha$-benzyloxycarbonyl-$N^\omega$-nitroarginine p-nitrophenylamide is treated with HBr in acetic acid to remove the benzyloxycarbonyl protecting group. The solvent is removed in vacuo and the product converted to the free base. Procedure 1-A is then followed substituting for $N^\alpha$-benzyloxycarbonyl-$N^\omega$-nitroarginine, the compound $N^\alpha$-benzyloxycarbonylalanine, and substituting for p-nitroaniline, the $N^\omega$-nitroarginine p-nitrophenylamide prepared as described above.

Alternatively, procedure 1-b may be followed substituting for $N^\alpha$-benzyloxycarbonyl-$N^\omega$-nitroarginine p-nitrophenyl ester, the compound N-benzyloxycarbonylalanine p-nitrophenyl ester and substituting for p-nitroaniline, the $N^\omega$-nitroarginine p-nitrophenylamide prepared as described above.

3. Reaction Step 3: Preparation of N-t-Butoxycarbonyl-γ-O-benzylglutamylalanyl-$N^\omega$-nitroarginine p-Nitrophenylamide The N-Benzyloxycarbonylalanyl-$N^\omega$-nitroarginine p-nitrophenylamide is treated with HBr in acetic acid to remove the benzyloxycarbonyl protecting group. The solvent is removed in vacuo and the product converted to the free base. Procedure 1-a is then followed substituting for $N^\alpha$-benzyloxycarbonyl-$N^\omega$-nitroarginine, the compound N-t-butoxycarbonyl-γ-O-benzylglutamic acid, and substituting for p-nitroaniline, the alanyl-$N^\omega$-nitroarginine p-nitrophenylamide prepared as described above.

4. Reaction Step 4: Preparation of N-Benzoylisoleucyl-γ-O-benzylglutamylalanyl $N^\omega$-nitroarginine p-Nitrophenylamide The N-t-butoxycarbonyl-γ-O-benzylglutamylalanyl-$N^\omega$-nitroarginine p-nitrophenylamide is added to TFA to remove the t-butoxycarbonyl group. The solvent is removed in vacuo and the product converted to the free base. Procedure 1-a is then followed substituting for $N^\alpha$-benzyloxycarbonyl-$N^\omega$-nitroarginine, the compound N-benzoylisoleucine and substituting for p-nitroaniline, the γ-O-benzyl-glutamylalanyl-$N^\omega$-nitroarginine p-nitrophenylamide prepared as described above.

Alternatively, procedure 1-b may be followed substituting for N$^\alpha$-benzyloxycarbonyl-N$^\omega$-nitroarginine p-nitrophenyl ester the compound N-benzoylisoleucine p-nitrophenyl ester, and substituting for p-nitroaniline, the γ-O-benzylglutamylalanyl-N$^\omega$-nitroarginine p-nitrophenylamide prepared as described above.

Alternatively, this compound may be prepared by method 1-a substituting for N$^\alpha$-benzyloxycarbonyl-N$^\omega$-nitroarginine, the compound N-benzoylisoleucyl-γ-O-benzylglutamic acid and substituting for p-nitroaniline, the alanyl-Nω-nitroarginine p-nitrophenylamide prepared as described in 3.

Alternatively, this compound may be prepared as described above but substituting N-t-butoxycarbonylisoleucine for N-benzoylisoleucine. The product is then converted to the final product by removing the N-t-butoxycarbonyl with TFA, then removing the TFA and treating the resulting compound with benzoyl chloride and a suitable base in a suitable solvent.

5. Reaction Step 5: Preparation of N-Benzoylisoleucylglutamylalanylarginyl p-Nitrophenylamide Hydrochloride The N-benzoylisoleucyl-γ-O-glutamylalanyl-N$^\omega$-nitroarginine p-nitrophenylamide is reacted with HF or boron-tris-trifluoroacetate in the presence of anisole or thioanisole. The solvent is removed in vacuo and the product purified by either HPLC, gel-filtration, ion-exchange, crystallization or a combination thereof.

B. METHOD 2

In this method, the guanido group of arginine is protected as its hydrochloride salt. This is then used as described in METHOD 1 in lieu of N$^\omega$-nitroarginine. Thus in METHOD 1 Reaction Step 1, for N$^\alpha$-benzyloxycarbonyl-N$^\omega$-nitroarginine is substituted N$^\alpha$-benzyloxycarbonylarginine hydrochloride. This gives N$^\alpha$-benzyloxycarbonylarginine p-nitrophenylamide hydrochloride which can be used in METHOD 1, Reaction Step 2, in place of N$^\alpha$-benzyl oxycarbonyl-N$^\omega$-nitroarginine. This gives N-benzyloxycarbonylalanylarginine p-nitrophenylamide hydrochloride which can be used in METHOD 1, Reaction Step 3, in place of N-benzyloxycarbonylalanyl-N$^\omega$-nitroarginine p-nitrophenylamide. This gives N-t-butoxycarbonyl-γ-O-benzylglutamylalanylarginine p-nitrophenylamide hydrochloride which can be used in METHOD 1, Reaction Step 4, in place of N-t-butoxycarbonyl-γ-O-benzylglutamylalanyl-N$^\omega$-nitroarginine p-nitrophenylamide. This gives N-benzoylisoleucyl γ-O-benzylglutamylalanylarginine p-nitrophenylamide hydrochloride which can be used in METHOD 1, Reaction Step 5, in place of N-benzoylisoleucyl-γ-O-benzylglutamylalanyl-N$^\omega$-nitroarginine p-nitrophenylamide. This gives the desired product N-benzoylisoleucylglutamylalanylarginine p-nitrophenylamide hydrochloride.

C. METHOD 3

Alternatively, other acid labile protecting groups can be used for protecting the guanidine of arginine in lieu of either the nitro or the hydrochloride, such as p-toluenesulfonyl or mesitylene-2-sulfonyl. These N$^\omega$-analogs can be substituted as described above to give the same product.

D. METHOD 4

Alternatively, the arginine can be added last to the peptide sequence. In this case, the tripeptide N-benzoylisoleucyl-γ-O-benzylglutamylalanine is made by standard peptide techniques referenced herein. This is coupled to arginine p-nitrophenylamide hydrochloride by methods described herein to give N-benzoylisoleucyl-γ-O-benzylglutamylarginine p-nitrophenylamide hydrochloride which is converted to product by methods described herein.

While the above reaction sequences detailed above are directed to certain specific substrates in accordance with the present invention, it will be appreciated by those of skill in the art that other substrates of the invention can be prepared by similar or analogous reaction sequences.

As was mentioned previously, the peptide-type compounds of the instant invention are particularly suited for use as substrates in LAL-type assay for detection of endotoxin. In such an assay, the endotoxin activated clot enzyme of LAL cleaves the subject substrates on the C-carboxyl of the arginine group to release a fluorogenic or chromogenic group such as p-nitroaniline. This cleavage allows for an indirect spectrophotometric determination of endotoxin due to the essential 1:1 proportionality that exists between the endotoxin activator and the pro-clot enzyme. More specifically, the amount of the terminal chromogenic or fluorogenic group of the compound which is enzymatically hydrolyzed or cleaved shows good correlation with the amount of endotoxin in a sample within a certain range, and the amount of the terminal group hydrolyzed increases proportionally to the increase in endotoxin content.

Quantitation of the activator (endotoxin) is not affected by the presence of excess substrate. The intact substrate has a maximum absorbence in the range in the range of 275–325 nm, whereas the cleaved $R_2BH$ marker compound has a different maximum absorbence, e.g., from about 360 to about 387. Therefore, the marker compound can be read at 405 nm without a substantial loss in sensitivity or interference from the intact peptide substrate.

The intact peptide absorption maximum has a molar extinction coefficient of about 11,984 at 312 nm; whereas its absorption at 405 nm is <200. However, the cleaved $R_2BH$ moiety such as p-nitroanaline, has a molar extinction of 10,500 at 380 nm and 8,438 at 405 nm. Therefore, the sensitivity of the test is not substantially affected. Thus, the concentration of a known endotoxin activator can be spectrophotometrically determined for a series of known concentrations such that a standard curve can be prepared. Thereby, such a curve can be used to determine the relative concentration of an endotoxin in an unknown test sample.

While the above description of the peptide-type compounds has been primarily directed to the detection and determination of the $R_2BH$ marker compound itself in an LAL assay, it is also within the scope of the present invention that the cleaved marker be coupled with another compound and the resultant coupled compound determined. For example, the marker compound 4-methoxy-β-naphthylamine, which can be determined fluorometrically, can be coupled to 5-nitrosalicylaldehyde and read spectrophotometrically at about 420–590 nm or can be coupled to O-dianisidine (fast blue B) and read spectrophotometrically at about 520 nm.

LAL may be prepared according to the procedure described in British Pat. No. 1,522,127 which is incorporated herein by reference. For example, the hemolymph from healthy specimens of *Limulus polyphemus* is collected in a saline anticoagulant solution generally described by Levin et al., "Clottable Protein in Limulus: Its Localization and Kinetics of Its Coagulation by Endotoxin", Thromb. Diath. Haemorrh 19: 186–197

(1968). The amebocytes are collected and washed with the saline anticoagulant solution and centrifuged. The separated amebocytes are then suspended in water and the osmotic disruption of the cells is complemented by multiple exposures to mechanical agitation. The cellular debris is separated from the lysate by means of a centrifuge and the lysate fractions are pooled and stored at 0°–4° C.

The sensitivity of the lysate toward endotoxin is adjusted to the desired level of sensitivity by dilution or by mixing with another batch of lysate of different sensitivity. The solution is generally buffered to the pH range 6.5–7.5 by means of a suitable buffer, e.g., tromethamine[tris-(hydroxymethyl)aminomethane] and tromethamine hydrochloride. The buffered lysate solution, prepared as described above, is subdivided into serum vials, and the subdivided solution is lyophilized. After lyophilization the vials are sealed and refrigerated. The lyophilized lysate has the form of a white powder or a white, frangible pellet.

Sensitivity of LAL toward endotoxin may be increased by including low concentrations of divalent cations such as calcium ions and monovalent cations such as sodium ions. The chloride salts, e.g., $CaCl_2$ and NaCl, are convenient sources of these added ions, although other salts may be used. The sensitivity of the LAL toward endotoxin may also be increased by the inclusion of certain amphoteric surfactants such as sulfobetaine surfacants as enhancing agents.

Methods for making peptide-type compounds in accordance with the present invention as well as the use of the compounds as substrates in an LAL-type assay are set forth in the following examples. It is to be understood that the examples are given for the purpose of illustration and do not limit the invention as has been heretofore described.

EXAMPLE I

The peptide substrate N-Benzoylisoleucyl-glutamylalanylarginine-p-nitroanilide hydrochloride (Bz-Ileu-Glu-Ala-Arg-pNA HCl) is prepared by the following reaction sequence:

A. Synthesis of the tripeptide fragment: N-benzoyl-L-isoleucine-γ-O-benzyl-L-glutamyl-L-alanine 1. t-BOC-L-Alanine 2,2,2-Trichloroethyl Ester t-BOC-L-Alanine was treated with N,N'-carbonyldiimidazole in DMF followed by 2,2,2-trichloroethanol. After the reaction was complete the solvent was removed, the residue dissolved in EtOAc and the EtOAc layer washed with water, dilute hydrochloric acid and 5% sodium bicarbonate. The EtOAc layer was dried with magnesium sulfate then evaporated to give the product.

2. t-BOC-γ-O-Benzyl-L-glutamyl-L-alanine 2,2,2-Trichloroethyl Ester

To the product from step 1 was added TFA. After reaction was complete, the TFA was evaporated. In a separate vessel was added t-BOC-γ-O-benzyl-L-glutamic acid, THF, N-methylmorpholine and isobutyl chloroformate under cooling. The residue from the TFA reaction was then added to this dissolved in THF. After the reaction was complete, the solvent was removed, EtOAc added and the EtOAc treated as in Step 1 to give the product.

3. t-BOC-L-Isoleucyl-γ-O-benzyl-L-glutamyl-L-alanyl 2,2,2-Trichloroethyl Ester

The product from Step 2 was treated with TFA. After the reaction was complete, the TFA was removed by evaporation. In a separate vessel was added t-BOC-L-isoleucine, THF, N-methylmorpholine, and isobutyl chloroformate under cooling. The residue from the TFA reaction was then added to this dissolved in THF. After the reaction was complete, the solvent was removed, EtOAc added and the EtOAc treated as in Step 1 to give the product.

4. N-Benzoyl-L-isoleucyl-γ-O-benzyl-L-glutamyl-L-alanine 2,2,2-Trichloroethyl Ester The product from Step 3 was added to TFA. When the reaction was complete, the TFA was removed by evaporation. In a separate vessel was added benzoic acid, THF, N-methylmorpholine and isobutyl chloroformate under cooling. The residue from the TFA reaction was then added to this dissolved in THF. After the reaction was complete, the solvent was removed by evaporation, EtOAc added and the EtOAc layer treated as was the EtOAc layer in Step 1 to give the product.

5. N-Benzoyl-L-isoleucyl-γ-O-benzyl-L-glutamyl-L-alanine

To the product from Step 4 was added acetic acid, water and zinc. When the reaction was complete, the solids were removed by filtration and the solvent removed by evaporation to give the above product.

B. N-Benzoyl-L-isoleucyl-γ-O-benzyl-L-glutamyl-L-alanyl-L-arginine p-Nitrophenylamide Hydrochloride To the product from Step 5 was added DMF, N-methylmorpholine, isobutyl chloroformate under cooling and then L-arginine p-nitrophenylamide dihydrochloride. After the reaction was complete, the solvent was removed by evaporation, chloroform added and the chloroform layer washed successively with water, dilute hydrochloric acid, 5% sodium bicarbonate and then dried with magnesium sulfate. The solvent was then removed by evaporation to give the product.

C. N-Benzoyl-L-isoleucyl-L-glutamyl-L-alanyl-L-arginine p-Nitrophenylamide Hydrochloride To the product from B was added hydrogen bromide in acetic acid. After the reaction was complete the solvent was removed by evaporation to give the product.

EXAMPLE II

Preparation of Limulus Lysate

A Limulus amebocyte lysate (LAL) formulation is prepared by a modified method of Levin et al. described in British Pat. No. 1,522,127. The lysate is modified by the addition of about 0.01M $MnCl_2$ and about 0.03% of a detergent sold under the trademark Zwittergent ™ 3-14. This formulation is lyophilized in 1.2 or 5.2 ml units.

EXAMPLE III

Activity of Various Substrates in a LAL Assay

An endotoxin of *E. coli*, Lot EC, obtained from the U.S. Food and Drug Administration, is reconstituted and diluted in water for injection to about 100 pg/ml. The endotoxin is used to activate the LAL by mixing about 0.1 ml of reconstituted LAL and about 0.1 ml of endotoxin with incubation at about 37° C. for about 15 minutes. The resulting amidase activity is measured by substrates of the present invention and by substrates that have been reported in U.S. Pat. No. 4,188,265 to be useful for a LAL-type assay.

The method used to measure the enzymatic activity of the activated LAL comprises adding about 0.1 ml of the LAL solution to about 0.5 ml of a 0.1 mM solution of substrate buffered by 0.05M Tris-Imidazole buffer at a pH of about 8.2 and containing about 0.04M CaCl$_2$. The solutions are mixed and incubated at about 37° C. After incubation of about six minutes, about 0.1 ml of a 50% solution of glacial acetic acid is added to terminate the reaction. The absorbence of the solution is then measured at 405 nm.

Table I shows the results for the activated LAL with the various substrates as measured by the concentration of hydrolyzed pNA. Substrate No. 1 (Bz-Ile-Glu-Gly-Arg-PNA) is taken as a standard and assumed to be 100% cleavable relative to the chromophore pNA.

TABLE I

Endotoxin Activated Limulus Amebocyte Enzyme as Measured with Various Substrates

| No. | SUBSTRATES | QUANTITY OF HYDRO-LYZED pNa (n moles) | RELA-TIVE ACTIV-ITY (%) |
|---|---|---|---|
| 1 | Bz—Ile—Glu—Gly—Arg—pNA | 7.48 | 100.00 |
| 2 | Bz—Ile—Glu—Ala—Arg—pNA | 7.06 | 94.38 |
| 3 | Bz—Ile—Glu—Cyst—Arg—pNA | 12.70 | 167.78 |
| 4 | Bz—Val—Gly—Arg—pNA | 7.28 | 97.32 |
| 5 | H—D-Val—Gly—Arg—pNA | 5.37 | 71.92 |
| 6 | Cbo—Val—Gly—Arg—pNA | <0.01 | <1.0 |
| 7 | Boc—Ala—Arg—pNA | <.01 | <1.0 |

Substrates number 2 and 3 are in accordance with the present invention. Based upon the quantity of hydrolyzed pNa, it is apparent that they are readily cleaved by the endotoxin activated LAL. Substrates 1 and 4 were designed to detect blood coagulation factor Xa and urokinase respectively. From the results of the activity of substrates numbers 4 and 6, it is evident that a change in the N-terminal blocking group of the Val-Gly-Arg-pNA sequence from Benzoyl to carbobenzoxy tends to block the amidase activity of the activiated LAL enzyme.

EXAMPLE IV

Determination of Activity Constants for Various Substrates

Using E. coli endotoxin 055:B5 (Difco Laboratories) diluted to about 0.250 ng/ml in water for injection, LAL is activated and used to determine Km (Michaelis-Menten constant) and Vmax for certain substrates according to this invention. Vmax is defined as the maximal observable velocity when all enzyme is present in the reaction mixture as an enzyme-substrate complex as depicted in the following reaction:

$$E + S \rightleftharpoons ES \rightleftharpoons E + P$$

E = Enzyme
S = Substrate
ES = Enzyme-substrate complex
P = Product

Km designates the substrate concentration that yields half-maximal velocity and is a measure of the affinity of the enzyme for a specific substrate. Km can be calculated using the following equation:

$$Km = \frac{([E] - [ES]) \cdot [S]}{[ES]}$$

Alternatively, Km and Vmax can be determined by mixing the activated enzyme with a buffered substrate and spectrophotometrically following the reaction for varied substrate concentrations. This alternative method was used to determine the Km and Vmax for substrates of this invention and two additional substrates for comparative purposes.

In determining Km and Vmax, a 0.2 ml aliquot of the endotoxin-activated LAL is mixed with about 0.7 ml of substrate buffered with 0.05M Tris-Imidazole at a pH of about 8.3 and containing about 0.04M CaCl$_2$ over a substrate concentration range of about 7 to 2,000 μM. The activated LAL and substrate are incubated at about 37° C. for about 3 minutes and the reaction is then terminated by the addition of about 0.2 ml of a 50% solution of glacial acetic acid. The reciprocal of the initial velocity 1/(v) as μM of formed hydrolyzed pNA/minute is plotted against 1/[S] in a diagram of the classical Lineweaver-Burk plot. Vmax and Km were determined from the plot and the results are tabulated in Table II.

TABLE II

The Kinetic Activity of Endotoxin-Activated LAL as Measured by Substrate Affinity (Km) and Enzyme Velocity (Vmax).

| No. | SUBSTRATE | Km (M) | Vmax $\left(\frac{\mu M}{L \ Minutes}\right)$ |
|---|---|---|---|
| 1 | Bz—Ile—Glu—Gly—Arg—pNa | $1.11 \times 10^{-4}$ | 40 |
| 2 | Bz—Val—Gly—Arg—pNA | $2.08 \times 10^{-4}$ | 46 |
| 3 | Bz—Ile—Glu—Ala—Arg pNA | $2.38 \times 10^{-4}$ | 240 |
| 4 | Bz—Ile—Gly—Cyst—Arg—pNA | $6.5 \times 10^{-4}$ | 117 |

As is apparent from the results presented in Table II, substrates numbers 3 and 4 in accordance with the present invention have a greater Vmax than the comparison substrates.

EXAMPLE V

Preparation of Standard Curves for an LAL Assay

Using E. coli endotoxin (0111:B4) and the substrates Bz-Ile-Glu-Ala-Arg-pNA and Bz-Ile-Glu-Cyst-Arg-pNA, the relationship between endotoxin concentration and hydrolyzed pNA was determined for each substrate. Initially, nine samples of endotoxin were diluted in water to provide solutions having a concentration range from about 0.0019 to about 0.500 ng/ml. About 0.1 ml of each endotoxin solution is mixed with about 0.1 ml of non-activated LAL and incubated for about 12-18 minutes. To this mixture is added about 0.7 ml of a 2 mM solution of substrate buffered by 0.05M Tris-Imidazole at a pH of 8.1 and containing about 0.04M of CaCl$_2$. The reaction is mixed and incubated at about 37° C. for about 3 minutes and then terminated by the addition of 0.2 ml of a 50% solution of glacial acetic acid. The absorbences of each of the solutions are then measured at 405 nm. Table III shows the results for the various endotoxin concentrations versus absorbence.

TABLE III

The Absorbence of hydrolyzed pNA from Substrates by Activated Limulus Lysate at Varying Levels of E. coli Endotoxin.
SUBSTRATE: Bz—Ile—Glu—Ala—Arg—pNA

| Endotoxin Concentration (pg/ml) | O.D. (405 nm) |
| --- | --- |
| 1.9 | 0.002 |
| 3.9 | 0.003 |
| 7.8 | 0.009 |
| 15.1 | 0.024 |
| 31.2 | 0.042 |
| 62.5 | 0.104 |
| 125.0 | 0.350 |
| 250.0 | 0.750 |
| 500.0 | 1.086 |
|  | 1.280 |
| 1.9 | 0.028 |
| 3.9 | 0.038 |
| 7.8 | 0.060 |
| 15.1 | 0.143 |
| 31.2 | 0.251 |
| 62.5 | 0.471 |
| 125.0 | 0.998 |
| 250.0 | 1.355 |
| 500.0 | 1.758 |

Plots of the data contained in Table III show the linearity of hydrolyzed pNA absorbence over a certain range of endotoxin concentration. More specifically, such curves illustrate that the substrates of this invention can be used to quantitatively detect endotoxin over at least a concentration range of about 7 to 125 pg/ml.

While the present invention has been described with reference to particular embodiments thereof, it will be understood that numerous modifications may be made by those skilled in the art without actually departing from the spirit and scope of the invention as defined in the appended claims.

It is claimed:

1. A method for the determination of endotoxin in a sample comprising contacting the sample with a pro-clotting enzyme from Limulus amebocyte lysate and a chromogenic or fluorogenic compound of the formula:

$$R_1-A_1-A_2-A_3-A_4-B-R_2$$

wherein $R_1$ represents hydrogen, a blocking aromatic hydrocarbon or acyl; $A_1$ represents an L or D-amino acid selected from Ileu, Val or Leu; $A_2$ represents Glu or Asp; $A_3$ represents Ala or Cyst; $A_4$ represents Arg; B represents a linkage group selected form ester and amide linkage groups; and $R_2$ represents a chromogenic or fluorogenic group which is covalently attached to the C-carboxyl terminal of arginine through the B linkage group, the fluorogenic or chromogenic moiety being capable of being enzymatically cleaved from the remainder of the peptide-type compound in the presence of endotoxin and pro-clotting enzyme to form at least part of a marker compound, and detecting the presence or absence of the marker compound in the sample.

2. A method according to claim 1 where B is an amide linkage.

3. A method according to claim 2 where $A_3$ is Ala.

4. A method according to claim 2 where $A_3$ is Cyst.

5. A method according to claims 3 or 4 wherein $A_2$ is Glu.

6. A method according to claims 3 or 4 wherein $A_2$ is Asp.

7. A method according to claim 5 wherein $A_1$ is Ileu.

8. A method according to claim 6 wherein $A_1$ is Val.

9. A method according to claim 8 wherein $R_2$ is p-nitrophenyl.

* * * * *